US008853463B2

(12) United States Patent
Karanjikar et al.

(10) Patent No.: US 8,853,463 B2
(45) Date of Patent: Oct. 7, 2014

(54) DECARBOXYLATION OF LEVULINIC ACID TO KETONE SOLVENTS

(71) Applicant: Ceramatec, Inc., Salt Lake City, UT (US)

(72) Inventors: Mukund Karanjikar, West Valley City, UT (US); Sai Bhavaraju, West Jordan, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 13/717,129

(22) Filed: Dec. 17, 2012

(65) Prior Publication Data
US 2014/0171688 A1 Jun. 19, 2014

Related U.S. Application Data

(63) Continuation-in-part of application No. 13/357,463, filed on Jan. 24, 2012, now Pat. No. 8,821,710.

(60) Provisional application No. 61/577,496, filed on Dec. 19, 2011, provisional application No. 61/436,088, filed on Jan. 25, 2011.

(51) Int. Cl.
C07C 45/41 (2006.01)
C25B 9/00 (2006.01)
C25B 3/00 (2006.01)
C07C 45/57 (2006.01)

(52) U.S. Cl.
CPC .. C07C 45/57 (2013.01); C25B 9/00 (2013.01)
USPC ............ 568/392; 568/397; 205/340; 205/462

(58) Field of Classification Search
USPC ................................... 568/392; 205/340, 462
See application file for complete search history.

(56) References Cited

U.S. PATENT DOCUMENTS

| 2,760,926 | A | 8/1956 | Kronenthal |
| 2,867,569 | A | 1/1959 | Kronenthal |
| 3,994,471 | A | 11/1976 | Turolla |
| 4,006,065 | A | 2/1977 | Meresz et al. |
| 4,123,336 | A | 10/1978 | Seko et al. |
| 4,402,804 | A | 9/1983 | Jackson |
| 4,464,236 | A | 8/1984 | Noding |
| 5,084,146 | A | 1/1992 | Huang |
| 5,290,405 | A | 3/1994 | Joshi et al. |
| 5,580,430 | A | 12/1996 | Balagopal et al. |
| 5,633,400 | A | 5/1997 | Wagner et al. |
| 5,841,002 | A | 11/1998 | Harrison et al. |
| 5,892,107 | A | 4/1999 | Farone et al. |
| 6,238,543 | B1 | 5/2001 | Law et al. |
| 6,362,380 | B1 | 3/2002 | Eicken et al. |
| 6,392,091 | B2 | 5/2002 | Lin |
| 2001/0019020 | A1 | 9/2001 | Merk et al. |
| 2005/0177008 | A1 | 8/2005 | Balagopal et al. |
| 2008/0177114 | A1 | 7/2008 | Goossen et al. |
| 2008/0245671 | A1 | 10/2008 | Balagopal et al. |
| 2009/0074611 | A1 | 3/2009 | Monzyk et al. |
| 2010/0159553 | A1 | 6/2010 | Bradin |
| 2010/0258447 | A1 | 10/2010 | Fan |
| 2010/0331170 | A1 | 12/2010 | Balagopal et al. |
| 2011/0024288 | A1 | 2/2011 | Bhavaraju et al. |
| 2011/0027848 | A1 | 2/2011 | Karanjikar et al. |
| 2011/0111475 | A1 | 5/2011 | Kuhry et al. |
| 2011/0168569 | A1 | 7/2011 | Bhavaraju et al. |
| 2011/0226633 | A1 | 9/2011 | Bhavaraju et al. |
| 2012/0123168 | A1 | 1/2012 | Putzig |
| 2012/0031769 | A1 | 2/2012 | Bhavaraju et al. |
| 2012/0142945 | A1 | 6/2012 | Hwang et al. |
| 2013/0001095 | A1 | 1/2013 | Bhavaraju et al. |

FOREIGN PATENT DOCUMENTS

| JP | 31-009458 | 11/1956 |
| JP | 06271499 | 9/1994 |
| SU | 979325 | 12/1982 |
| WO | WO-2007/095215 | 8/2007 |
| WO | WO-2011011492 | 1/2011 |

OTHER PUBLICATIONS

Palit, Santi R., "The Solubility of Soaps and of Some Salts in Mixtures of Solvents, One of Which Is of Glycolic Type", Utah Consortia UALC, vol. 69, (Dec. 1947),3120-29.
Park, Sang Ho "PCT International Search Report", Int. App. No. PCT/US2010/042715, (Apr. 29, 2011),1-3.
Park, Sang Ho "PCT Written Opinion", Int. App. No. PCT/US2010/042715, (Apr. 29, 2011),1-4.
Kang, Sang Yoon "PCT International Search Report", Int. App. No. PCT/US2010/042756, (Feb. 28, 2011),1-3.
Kang, Sang Yoon "PCT Written Opinion", Int. App. No. PCT/US2010/042756, (Feb. 28, 2011),1-4.
Park, Sang Ho "PCT International Search Report", Int. App. No. PCT/US2010/042780, (May 2, 2011),1-3.
Park, Sang Ho "PCT Written Opinion", Int. App. No. PCT/US2010/042780, (May 2, 2011),1-4.
Bozell, Joseph J., "Connecting Biomass and Petroleum Processing with a Chemical Bridge", Science, (Jul. 30, 2010),vol. 329: 522-523.
Bond, Jesse Q., et al., "Integrated Catalytic Conversion of gamma-Valerolactone of Liquid Alkenes for Transportation Fuels", Science, (Feb. 26, 2010),vol. 327: 1110-1114.

(Continued)

Primary Examiner — Sikarl Witherspoon
(74) Attorney, Agent, or Firm — David Fonda

(57) ABSTRACT

Ketones, specifically Methyl ethyl ketone ("MEK") and octanedione, may be formed from six carbon sugars. This process involves obtaining a quantity of a six carbon sugar and then reacting the sugar to form levulinic acid and formic acid. The levulinic acid and formic acid are then converted to an alkali metal levulinate and an alkali metal formate (such as, for example, sodium levulinate and sodium formate.) The alkali metal levulinate is placed in an anolyte along with hydrogen gas that is used in an electrolytic cell. The alkali metal levulinate within the anolyte is decarboxylated to form MEK radicals, wherein the MEK radicals react with hydrogen gas to form MEK, or MEK radicals react with each other to form octanedione. The alkali metal formate may also be decarboxylated in the cell, thereby forming hydrogen radicals that react with the MEK radicals to form MEK.

23 Claims, 7 Drawing Sheets

(56) References Cited

OTHER PUBLICATIONS

Chum, H L., et al., "Photoelectrochemistry of Levulinic Acid on Undoped Platinized n-TIO2 Powders", *J. Phys. Chem*, (1983),vol. 87: 3089-3093.

Schafer, Hans-Jurgen "Recent Contributions of Kolbe Electrolysis to Organic Synthesis", *Topics in Current Chemistry*, (1990),vol. 152: 91-151.

Rabjohn, et al., "Kolbe Electrosynthesis of Alkanes with Multiple Quaternary Carbon Atoms", *J. Org. Chem.*, (1981),vol. 46, pp. 4082-4083.

Wong, Edna "USPTO Office Action", U.S. Appl. No. 12/840,508, (Nov. 2, 2011),17 pages.

Kobzeva, et al., "Effect of a solvent on anode processes", *Elektrokhimiya*, vol. 11. No. 5, (1975),1 page abstract.

Ono, et al., "Electrolysis of fatty acids I", *Ind. Chem. Sect. 53*, (1950),1 page abstract.

Minami, et al., "Electrolysis of Fatty Acids II", *Kogyo Kagaku Zasshi*, vol. 53, (1950),1 page abstract.

Obermuller, "Saponification by Sodium Ethoxide", *J Chem. Soc., Abstr. 62*, (1892),1 page abstract.

Wong, Edna "USPTO Office Action", U.S. Appl. No. 12/840,913, (Nov. 16, 2011),16 pages.

Wong, Edna "Non-Final Office Action", U.S. Appl. No. 12/840,508, (Apr. 26, 2012),1-32.

Wong, Edna "Non-Final Office Action", U.S. Appl. No. 12/840,913, (Apr. 10, 2012),1-12.

Mendez, Zulmariam "Non-Final Office Action", U.S. Appl. No. 12/840,401, (Jun. 5, 2012),1-12.

Wong, Edna "Non-Final Office Action", U.S. Appl. No. 13/357,463, (Jun. 4, 2012),1-25.

Pande, et al., "Studies on Kolbe's Electrosynthesis", *Electrochimica Acta*, Aug. 1961, vol. 4,215-231.

Ho, Park S., "International Search Report", PCT US 2011/035782 (corresponding to U.S. Appl. No. 13/103,716, (Feb. 9, 2012),1-3.

Ho, Park S., "Written Opinion of the International Searching Authority", PCT US 2011/035782 (corresponding to U.S. Appl. No. 13/103,716, (Feb. 9, 2012),1-4.

Ko, et al., "Computer Translation of the Detailed Description of JP 6-271499", *Japanese Patent publication 06-271499*, (Sep. 27, 1994),1-8.

Aslanov, N. N. "English Language Bibliographical Information and Abstract", SU Patent No. 979325, (Dec. 7, 1982),1-3.

Choi, et al., "Recovery of lactic acid from sodium lactate by ion substitution using ion-exchange membrane", *Separation and Purification Technology 28* (2002), Elsevier, (Mar. 4, 2002),69-79.

Habova, et al., "Application of Electrodialysis for Lactic Acid Recovery", *Czech J. Food Sci.*, vol. 19, No. 2 (2001), (Jan. 1, 2001),73-80.

Huang, et al., "Application of electrodialysis to the production of organic acids: State-of-the-art and recent developments", *Journal of Membrane Science 288* (2007), Elsevier, (Nov. 25, 2006),1-12.

Lu, et al., "Modeling of the mass transfer and conduction behavior in electro-electrodialysis with oil/water emulsion as the catholyte", *Journal of Membrane Science 322* (2008), Elsevier, (Jun. 5, 2008),265-274.

Moon, et al., "Competitive Anion Transport in Desalting Mixtures of Organic Acids by Batch Electrodialysis", *Journal of Membrane Science 141* (1998), Elsevier, (Apr. 1, 1998),75-89.

Palaty, et al., "Continuous dialysis of carboxylic acids. Permeability of Neosepta-AMH membrane", *Desalination 216* (2007), Elsevier, (Oct. 1, 2007),345-355.

Prado Rubio, et al., "Modeling Reverse Electro-Enhanced Dialysis for Integration with Lactic Acid Fermentation", *CAPEC, Department of Chemical and Biochemical Engineering Technical University of Denmark (DTU)*, DK-2800 Lyngby, Denmark, 2009, Available as "A-DK-Prado Rubio-OA-1" at Docstoc.com, http://www.docstoc.com/search/modeling%20reverse%20electro-enhanced%20dialysis%20for%20integration%20with%20lactic%20acid%20fermentation?catid=0,(Jan. 1, 2009),1-2.

Yi, et al., "An in situ coupling separation process of electro-electrodialysis with back-extraction", *Journal of Membrane Science 255* (2005), Elsevier, (Mar. 21, 2005),57-65.

Conway, et al., "New Approaches to the Study of Electrochemical Decarboxylation and the Kolbe Reaction. I. The Model Reaction with Formate", *Canadian Journal of Chemistry*(no month, 1963), vol. 41, (1963),21-37.

Wong, Edna "Final Office Action", U.S. Appl. No. 12/840,913, (Aug. 14, 2012),1-28.

Wong, Edna "Final Office Action", U.S. Appl. No. 12/840,508, (Nov. 27, 2012),1-25.

Wong, Edna "Final Office Action", U.S. Appl. No. 13/357,463, (Sep. 19, 2012),1-17.

Park, Sang H., "International Search Report", PCT Application No. PCT/US2011/033626 (corresponding to U.S. Appl. No. 13/092,685, (Feb. 8, 2012),1-3.

Park, Sang H., "Written Opinion of the International Searching Authority", PCT Application No. PCT/US2011/033626 (corresponding to U.S. Appl. No. 13/092,685, (Feb. 8, 2012),1-4.

Paul, et al., "Reactions of Sodium Metal with Aromatic Hydrocarbons", *J. Am. Chem. Soc.*, 1956, 78 (1), (Jan. 1956),116-120.

Dzik, et al., "Carboxylates as sources of carbon nucleophiles and electrophiles: comparison of decarboxylative and decarbonylative pathways", *Chemical Science*, 2012, vol. 3, Issue No. 9 (2012), (May 3, 2012),2671-78.

Mendez, Zulmariam "Final Office Action", U.S. Appl. No. 12/840,401, (Mar. 15, 2013),1-12.

Wong, Edna "Non Final Office Action", U.S. Appl. No. 12/840,913, (Mar. 28, 2013),1-31.

Sekine, Isao et al., "Effect of the Concentration of Acetate or Propionate on the Abnormal Phenomena in the Kolbe Reaction", *Denki Kagaku*, vol. 41(9), (1973),702-707.

Wong, Edna "Non Final Office Action", U.S. Appl. No. 13/357,463, (Apr. 9, 2013),1-21.

Kang, Tai H., "Written Opinion of the International Searching Authority", PCT/US2012/070154 (corresponding to U.S. Appl. No. 13/717,129), (Apr. 22, 2013),1-3.

Kang, Tai H., "International Search Report", PCT/US2012/070154 (corresponding to U.S. Appl. No. 13/717,129), (Apr. 22, 2013),1-4.

Fonda, David "Explanation of Relevance for JP 31-009458", Applicants' Concise Explanation of Relevance for JP 31-009458 (cited in PCT/US2012/070154 Search Report), (May 14, 2013),1.

DECARBOXYLATION OF LEVULINIC ACID TO KETONE SOLVENTS

RELATED APPLICATION

This application claims the benefit of U.S. Provisional Patent Application No. 61/577,496, filed on Dec. 19, 2011 and is a continuation in part of, and claims priority to, U.S. patent application Ser. No. 13/357,463 filed Jan. 24, 2012, which application claimed priority to U.S. Provisional Patent Application No. 61/436,088 filed Jan. 25, 2011. This applications are expressly incorporated herein by reference.

BACKGROUND OF THE INVENTION

The present invention describes a method for the manufacture of ketone solvents, such as methyl ethyl ketone ("MEK") or octanedione. MEK has a chemical formula of $$CH_3-C(O)-CH_2CH_3.$$

This chemical is valuable as an organic solvent and is used as a solvent in many commercial manufacturing processes. MEK is also used in some household products such as varnish and lacquer.

Unfortunately, MEK can be expensive to produce. Thus, a new method for manufacturing MEK is desirable. Such a method is disclosed herein.

BRIEF SUMMARY OF THE INVENTION

Levulinic acid is an organic acid that is cheaply produced from naturally occurring hexose sugar materials. As is known in the art, hexose sugar materials include one or more rings. Hexose sugar materials include six (6) carbon atoms. Examples of these types of sugar materials include glucose, etc.

Specifically, a sugar monomer, which has the formula $C_6H_{12}O_6$ may be reacted as follows to form levulinic acid, water and formic acid:

$$C_6H_{12}O_6 \longrightarrow C_5H_8O_3 + HCOOH + H_2O$$
(sugar monomer) (levulinic acid) (Formic acid) (water)

$C_5H_8O_3$ is the empirical formula of levulinlic acid. However, this acid has the following chemical structure:

$$CH_3-C(O)-CH_2CH_2COOH$$

Once these two acids (levulinic acid and formic acid) are obtained, these two acids may be saponified by reaction with a base (such as NaOH, NaOCH$_3$, or any other base) to form the corresponding alkali metal salt (e.g., alkali metal salts of formate and levulinate):

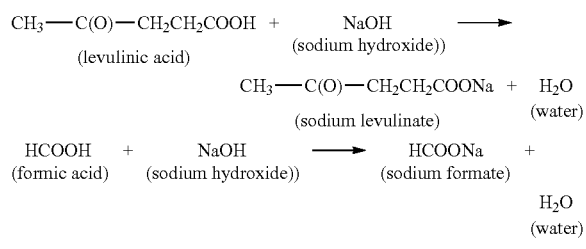

Once the alkali metal salts of formate and levulinate have been formed, a decarboxylation reaction may be performed using an electrochemical cell. Specifically, the formate and levulinate anions are part of an anolyte solution (that also includes a solvent such as water or methanol) and are reacted as follows:

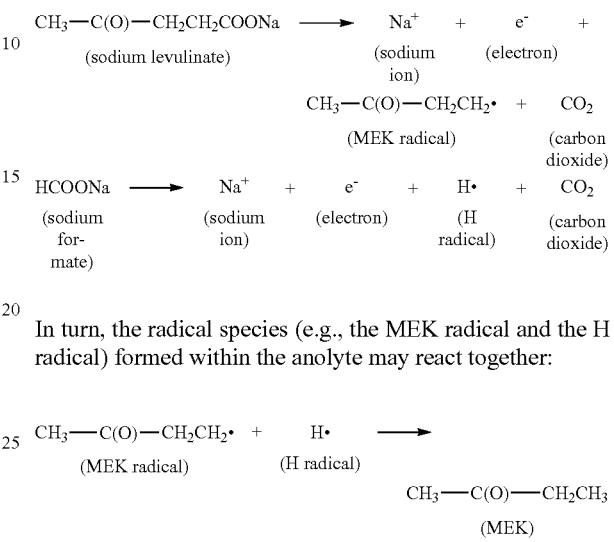

In turn, the radical species (e.g., the MEK radical and the H radical) formed within the anolyte may react together:

$$CH_3-C(O)-CH_2CH_2\cdot + H\cdot \longrightarrow$$
(MEK radical) (H radical)
$$CH_3-C(O)-CH_2CH_3$$
(MEK)

Alternative embodiments may be designed in which formic acid is not used as the source of the H. that reacts with the MEK radical. For example, in other embodiments, hydrogen radicals may be created by a Pd anode, by photolysis of hydrogen gas, from Pd and pressurized hydrogen gas, or from another species that donates the H radical (such as an alkane or other organic material).

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the present embodiments, as represented in the Figures, is not intended to limit the scope of the invention, as claimed, but is merely representative of presently preferred embodiments of the invention.

Figure 1:
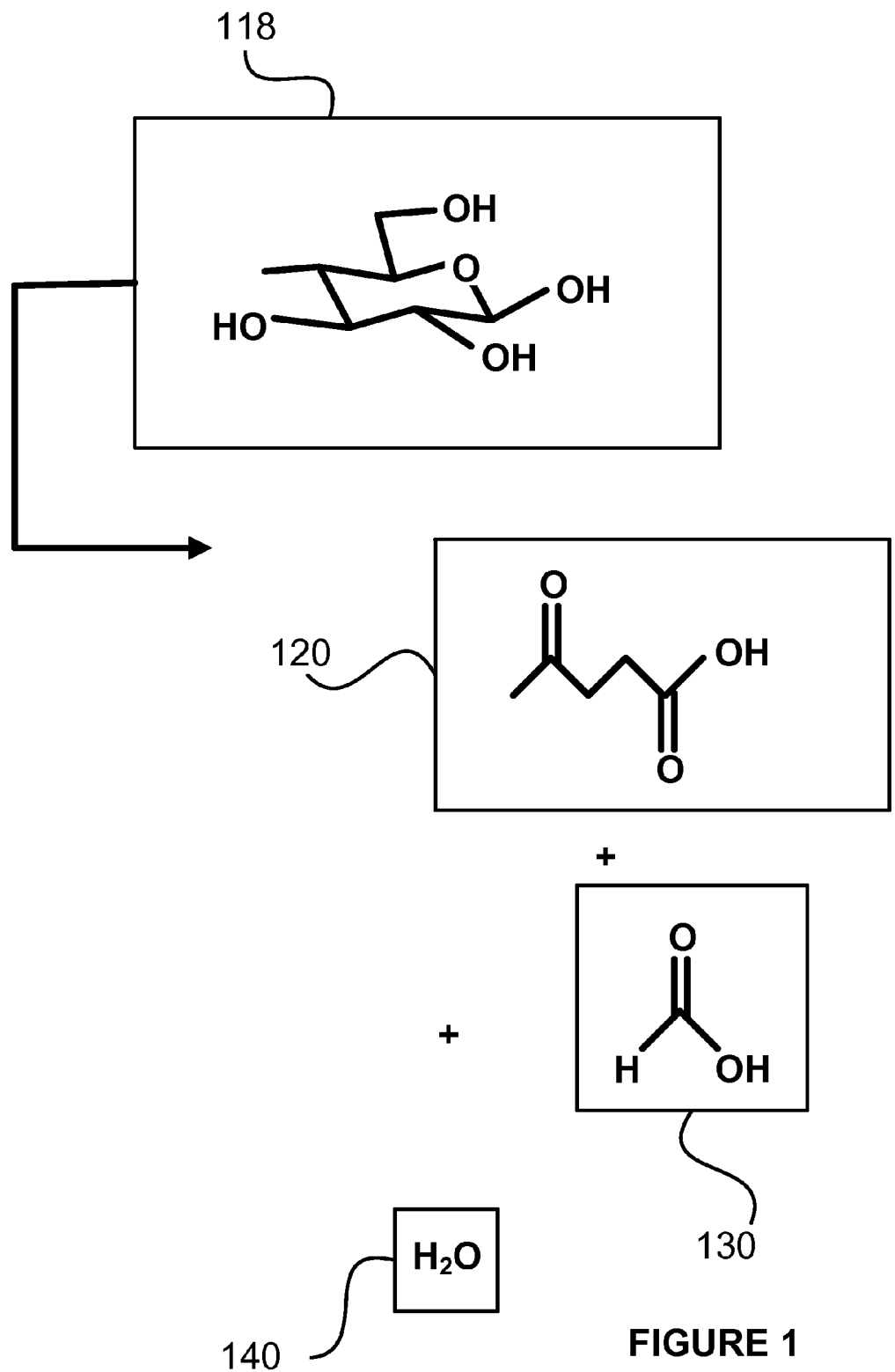
FIG. 1 is a flow diagram showing the conversion of sugar moieties into levulinic acid and formic acid.

Referring now to FIG. 1, the process for converting sugar moieties into levulinic acid is described. Specifically, this process may involve converting a hexose sugar 118 (such as glucose, etc.) into levulinic acid. One example of the process is described in the following article:

Bozell J., Connecting Biomass and Petroleum Processing with a Chemical Bridge, Science, Vol. 239, pp 522-523, (2010).

This process is a dehydration reaction as water is produced. The dehydration of a sugar 118, which is performed by treatment with acid, ultimately forms levulinic acid 120 and formic acid 130 in an approximately 3:1 weight ratio. (Water 140 is also formed.) This transformation has been known for decades. Accordingly, those skilled in the art are familiar with the processes needed to create levulinic acid. Further information regarding the production of levulinic acid is found in the following article:

Bond, Jesse Q., et al., Integrated Catalytic Conversion of γ-Valerolactone to Liquid Alkenes for Transportation Fuels, Science 327, 1110-1114 (2010).

Figure 1A:
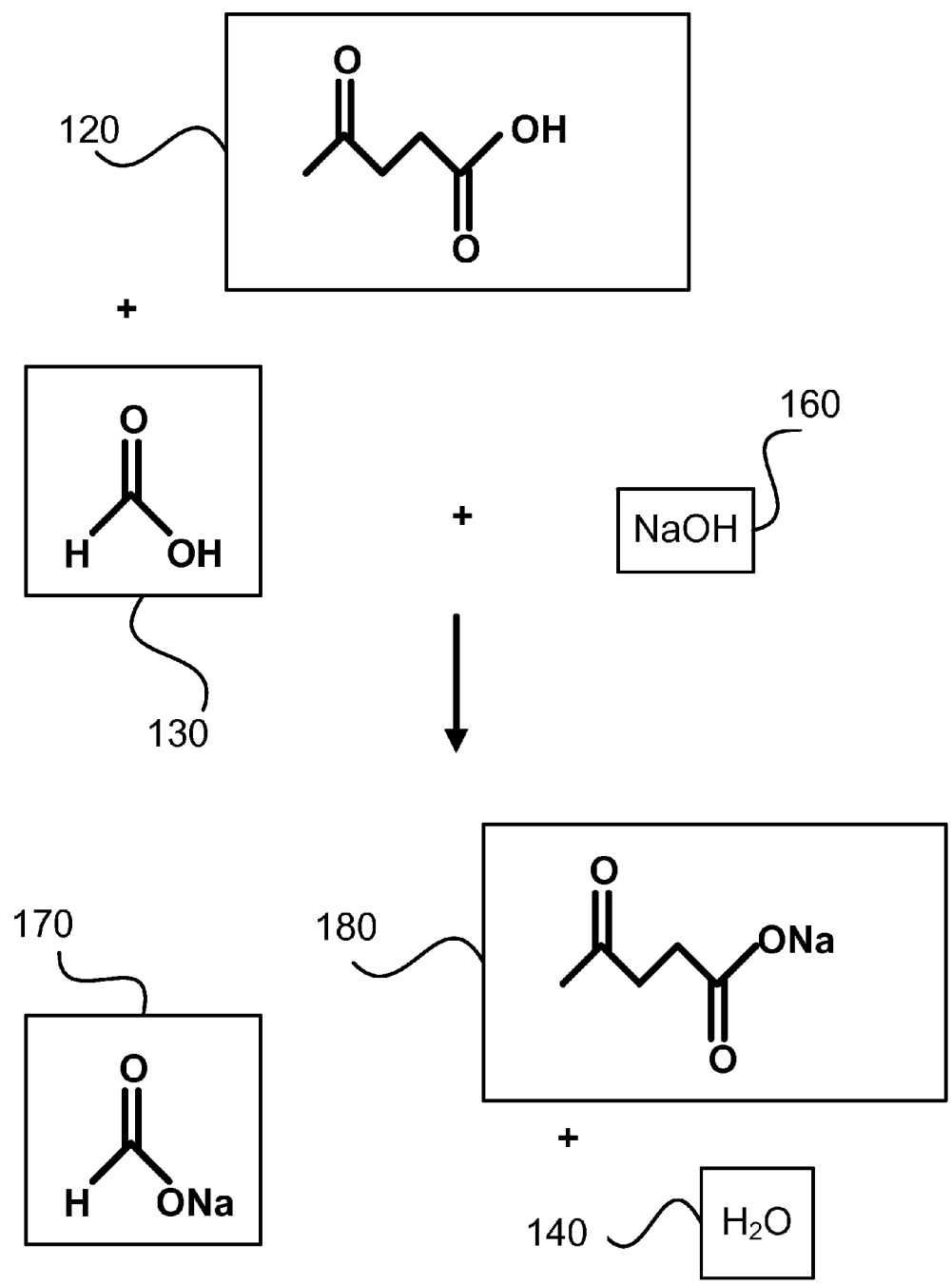
FIG. 1A is a flow diagram showing the conversion of levulinic acid and formic acid to sodium formate and sodium levulinate.

In turn, levulinic acid may be used in an electrochemical cell. However, prior to using the levulinic acid in an electrochemical cell, the levulinic acid may be converted to an alkali metal salt using a saponification reaction as shown in FIG. 1A. The saponification reaction involves reacting the levulinic acid 120 and/or the formic acid 130 with a base 160. In FIG. 1A, the base 160 is NaOH. However, other bases may be used (such as sodium methoxide, sodium ethoxide, KOH, potassium methoxide, etc.) This saponification reaction produces water 140, sodium formate 170 and sodium levulinate 180, all of which may remain in the anolyte. Of course, instead of sodium, another alkali metal may be used as the corresponding cation.

Electrochemical cells have been used to conduct various chemical reactions. The electrochemical cell will generally have an anode and a cathode. Typically, the anode may be made of smooth platinum, stainless steel, or may be a carbon based electrode. Examples of carbon based electrodes include boron doped diamond, glassy carbon, synthetic carbon, Dimensionally Stable Anodes (DSA), and lead dioxide. Other materials such as Pd may also be used for the electrode.

At the anode of the electrochemical cell, various reactions may occur. One type of these reactions is referred to as the "Kolbe reaction." This reaction involves an oxidation (decarboxylation) step. Specifically, in the standard Kolbe reaction, anodic decarboxylation/oxidative coupling of carboxylic acids occurs. This reaction is a free radical reaction and is shown below:

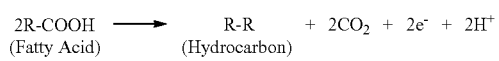

This Kolbe reaction is typically conducted in non-aqueous methanolic solutions, with partially neutralized acid (in the form of alkali salt) used with a parallel plate type electrochemical cell. The anolyte used in the cell may have a high density. The Kolbe reaction has been known and used. In fact, the following article summarizes and explains the Kolbe reaction:

Hans-Jurgen Schafer, Recent Contributions of Kolbe electrolysis to organic synthesis, Topics in Current Chemistry, Vol. 153, Issue: Electrochemistry IV, 1990, pp. 91-151.

As can be seen from the Kolbe reaction, the "R" groups of two fatty acid molecules are coupled together, thereby resulting in a hydrocarbon product. The Kolbe reaction is a free radical reaction in which two "R radicals" (R.) are formed and are subsequently combined together to form a carbon-carbon bond.

The present embodiments relate to a modified "Kolbe" reaction. Specifically, the present embodiments involve decarboxylation to form an "R radical" (R.) (such as the MEK radical). Hydrogen radicals may be added/formed to couple with the MEK radical, thereby forming MEK.

As noted above, sodium levulinate may be decarboxylated at the anode of a cell to produce an MEK radical. This reaction may be represented as follows:

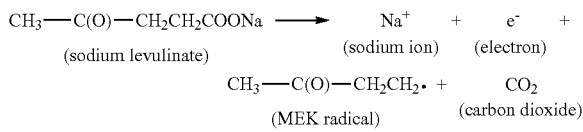

This MEK radical may then be reacted with a H radical (H.) to form the MEK. This H radical (H.) may be formed in a variety of different ways, including the decarboxylation of sodium formate:

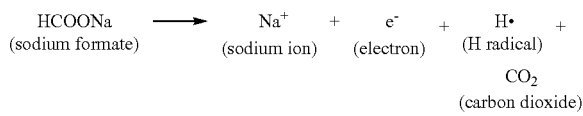

Thus, when a solution containing formate and levulinate are decarboxylated together, the H radicals and the MEK radicals may react together to form MEK.

Figure 2:
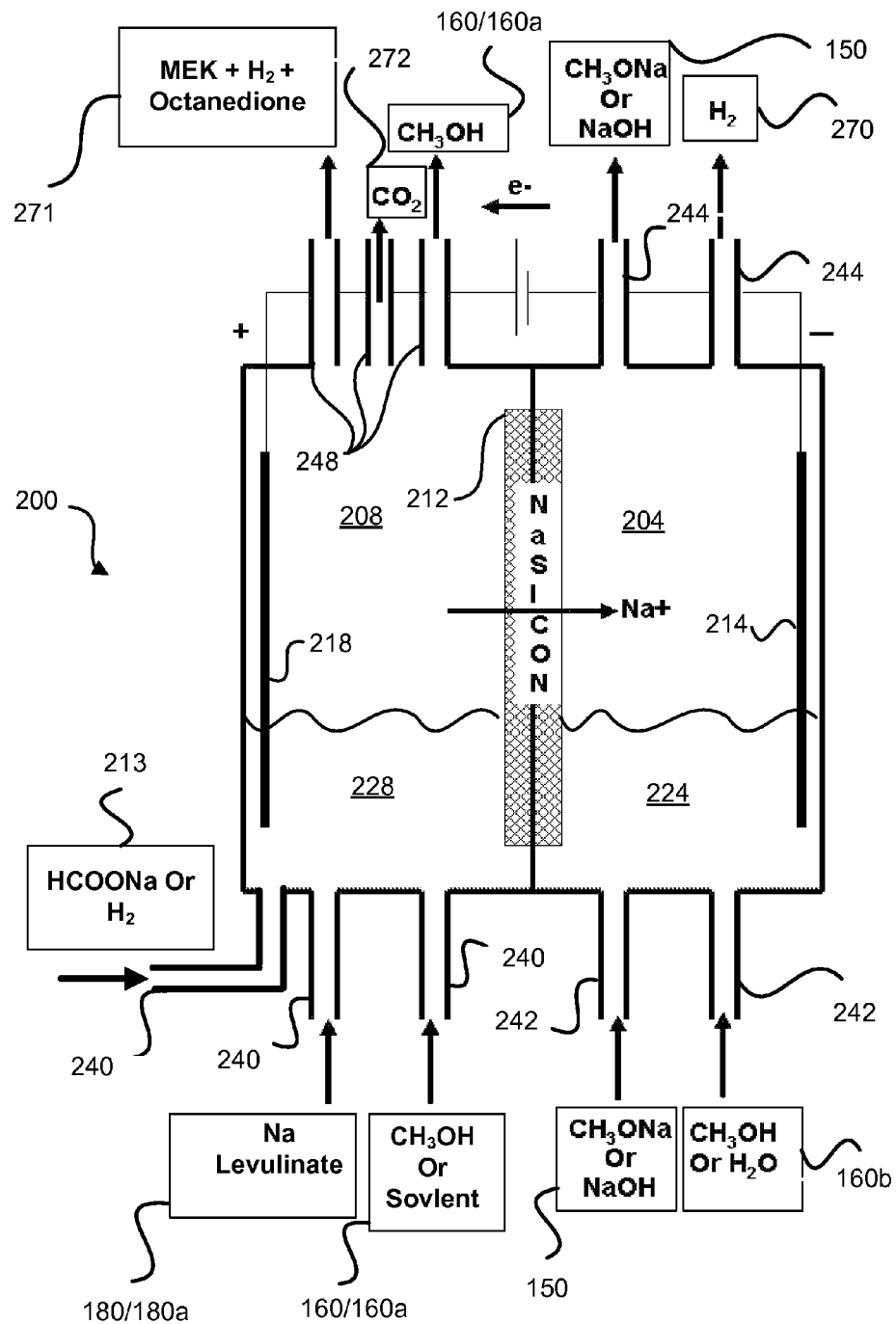
FIG. 2 is a schematic view of an embodiment of an electrolytic cell for conversion of sodium levulinate to MEK and other products.

Referring now to FIG. 2, an electrochemical cell is shown 200 to which a voltage may be applied. The advanced Kolbe reaction discussed above occurs within the electrochemical cell 200. The cell 200 includes a catholyte compartment 204 and an anolyte compartment 208. The catholyte compartment 204 and the anolyte compartment 208 may be separated by a membrane 212. Other embodiments may be designed in which there is only a single compartment that houses both the anode and the cathode.

The particulars of each cell 200 will depend upon the specific embodiment. For example, the cell 200 may be a standard parallel plate cell, where flat plate electrodes and/or flat plate membranes are used. In other embodiments, the cell 200 may be a tubular type cell, where tubular electrodes and/or tubular membranes are used. An electrochemically active anode 218 is housed, at least partially or wholly, within the anolyte compartment 208. More than one anode 218 may also be used. The anode 218 may comprise, for example, a smooth platinum electrode, a stainless steel electrode, or a carbon based electrode. Examples of a typical carbon based electrode include boron doped diamond, glassy carbon, synthetic carbon, Dimensionally Stable Anodes (DSA) and relatives, and/or lead dioxide. Other electrodes may comprise metals and/or alloys of metals, including S.S, Kovar, Inconel/monel. Other electrodes may comprise $RuO_2$—$TiO_2$/Ti, $PtO_x$—$PtO_2$/Ti, $IrO_x$, $Co_3O_4$, $MnO_2$, $Ta_2O_5$ and other valve metal oxides. In addition, other materials may be used to construct the electrode such as $SnO_2$, $Bi_2Ru_2O_7$ (BRO), $BiSn_2O_7$, noble metals such as platinum, titanium, palladium, and platinum clad titanium, carbon materials such as glassy carbon, BDD, or Hard carbons. Additional embodiments may have $RuO_2$—$TiO_2$, hard vitrems carbon, and/or $PbO_2$. Again, the foregoing serve only as examples of the type of electrodes that may be employed. The cathode compartment 204 includes at least one cathode 214. The cathode 214 is partially or wholly housed within the cathode compartment 204. The material used to construct the cathode 214 may be the same as the material used to construct the anode 218. Other embodiments may be designed in which a different material is used to construct the anode 218 and the cathode 214.

The anolyte compartment 208 is designed to house a quantity of anolyte 228. The catholyte compartment 204 is designed to house a quantity of catholyte 224. In the embodiment of FIG. 2, the anolyte 228 and the catholyte 224 are both liquids, although solid particles and/or gaseous particles may also be included in either the anolyte 228, the catholyte 224, and/or both the anolyte 228 and the catholyte 224.

The anode compartment 208 and the cathode compartment 204 are separated by an alkali metal ion conductive membrane 212. The membrane utilizes a selective alkali metal transport membrane. For example, in the case of sodium, the membrane is a sodium ion conductive membrane 212. The sodium ion conductive solid electrolyte membrane 212 selectively transfers sodium ions ($Na^+$) from the anolyte compartment 208 to the catholyte compartment 204 under the influence of an electrical potential, while preventing the anolyte 228 and the catholyte 224 from mixing. Examples of such solid electrolyte membranes include those based on NaSICON structure, sodium conducting glasses, beta alumina and solid polymeric sodium ion conductors. Such materials are commercially available. NaSICON typically has a relatively high ionic conductivity at room temperature. Alternatively, if the alkali metal is lithium, then a particularly well suited material that may be used to construct an embodiment of the membrane is LiSICON. Alternatively, if the alkali metal is potassium, then a particularly well suited material that may be used to construct an embodiment of the membrane is KSICON.

As noted above, the saponification reaction shown in FIG. 1A (and/or other reactions) are designed to produce a quantity of an alkali metal salt of levulinic acid 180 (e.g., sodium levulinate). This alkali metal salt of a levulinic acid 180 may be separated and/or purified, as needed Likewise, as desired, if the alkali metal salt of levulinic acid 180 comprises a mixture of fatty acid salts, these compounds may be separated. Alternatively, the alkali metal salt of levulinic acid 180 may not be separated and may comprise a mixture of different salts.

The anolyte compartment 208 may include one or more inlets 240 through which the anolyte 228 may be added. Alternatively, the components that make up the anolyte 228 may be separately added to the anolyte compartment 208 via the inlets 240 and allowed to mix in the cell. The anolyte includes a quantity of the alkali metal salt of levulinic acid 180. In the specific embodiment shown in FIG. 2, sodium is the alkali metal, so that alkali metal salt of levulinic acid 180 is a sodium salt 180a. The anolyte 228 also includes a first solvent 160, which as noted above, may be an alcohol, such as methyl alcohol 160a. Of course, other types of solvents may also be used.

The catholyte compartment 204 may include one or more inlets 242 through which the catholyte 224 may be added. The catholyte 224 includes a second solvent 160b. The second solvent 160b may be an alcohol or water (or a mixture of alcohol and water). As shown in FIG. 2, the alcohol is methyl alcohol. Significantly, the solvent 160b in the catholyte 224 may not necessarily be the same as the first solvent 160a in the anolyte 228. In some embodiments, the solvents 160a, 160b may be the same. The reason for this is that the membrane 212 isolates the compartments 208, 204 from each other. Thus, the solvents 160a, 160b may be each separately selected for the reactions in each particular compartment (and/or to adjust the solubility of the chemicals in each particular compartment). Thus, the designer of the cell 200 may tailor the solvents 160a, 160b for the reaction occurring in the specific compartment, without having to worry about the solvents mixing and/or the reactions occurring in the other compartment. This is a significant advantage in designing the cell 200. A typical Kolbe reaction only allows for one solvent used in both the anolyte and the catholyte. Accordingly, the use of two separate solvents may be advantageous. In other embodiments, either the first solvent 160a, the second solvent 160b, and/or the first and second solvents 160a, 160b may comprise a mixture of solvents.

The catholyte 224 may also include a base 150. In the embodiment of FIG. 1, the base 150 may be NaOH or sodium methoxide, or a mixture of these chemicals. The base 150 may be the same base 150 as used in the saponification reaction of FIG. 1A. Alternatively, the base may be a different base than that which was used in the saponification reaction.

The anolyte 228 may also include a hydrogen supplier 213 that may be added through an inlet 240. The hydrogen suppler 213 may comprise hydrogen gas in some embodiments. Additionally or alternatively, the hydrogen supplier 213 may be sodium formate. Other chemicals may also be used as the hydrogen supplier 213. The hydrogen supplier 213 may be introduced into the anolyte such that it mixes with the solvent 160 and alkali metal salt of levulinic acid 180 within the anolyte compartment 208. Alternatively, the hydrogen suppler 213 may be pre-mixed with the alkali metal salt of levulinic acid 180 and/or the solvent prior to entering the anolyte compartment 208.

The reactions that occur at the anode 218 and cathode 214 will now be described. As with all electrochemical cells, such reactions may occur when a voltage is applied to the cell 200.

At the cathode 214, a reduction reaction takes place. This reaction uses sodium ions from the solvent and the solvent to form hydrogen gas 270 as well as an additional quantity of base 150. Using the chemicals of FIG. 2 as an example, the reduction reaction(s) may be written as follows:

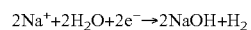
$2Na^+ + 2H_2O + 2e^- \rightarrow 2NaOH + H_2$

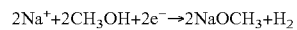
$2Na^+ + 2CH_3OH + 2e^- \rightarrow 2NaOCH_3 + H_2$

The hydrogen gas 270 and/or the base 150 may be extracted through outlets 244. The hydrogen gas 270 may be gathered for further processing for use in other reactions, and/or disposed of or sold. The production of the base 150 is a significant advantage because the base 150 that was consumed in the saponification reaction of FIG. 1A is generated in this portion of the cell 200. Thus, the base formed in the cell may be collected and re-used in future saponification reactions (or other chemical processes). As the base may be re-used, the hassle and/or the fees associated with disposing of the base are avoided.

The reactions that occur at the anode 218 may involve decarboxylation. These reactions may involve an advanced Kolbe reaction (which is a free radical reaction) to form a quantity of a product 271 and carbon dioxide 272. The solvent 160/160a may also be recovered and recycled, if desired, back to the inlet 240 for future use.

Using the chemicals of FIG. 2 as an example, the oxidation reactions may be written as follows:

$$CH_3-C(O)-CH_2CH_2COONa \longrightarrow CH_3-C(O)-CH_2CH_2\bullet +$$
(Sodium levulinate) (MEK radical)
$$CO_2 + e^- + Na^+$$

The carbon dioxide 272 may be vented off (via one or more outlets 248). This is a safe, naturally-occurring chemical that may be collected, disposed of, or re-used. Further, if the hydrogen generator 213 is sodium formate, then the following Kolbe reaction will also occur:

$$HCOONa \longrightarrow Na^+ + e^- + H\bullet +$$
(sodium formate) (sodium ion) (electron) (H radical)
$$CO_2$$
(carbon dioxide)

The advanced Kolbe reaction may comprise a free radical reaction. As such, the reaction produces (as an intermediate) a MEK radical designated as $CH_3-C(O)-CH_2CH_2\bullet$. Radical species are highly reactive. Accordingly, when two of these MEK radicals react together, the following product is formed:

$$CH_3-C(O)-CH_2CH_2\bullet + CH_3-C(O)-CH_2CH_2\bullet \longrightarrow$$
(MEK radical) (MEK radical)
$$CH_3-C(O)-CH_2CH_2-CH_2CH_2-C(O)-CH_3$$
(octanedione)

As shown in FIG. 2, this octanedione makes up a portion of the product 271. However, as noted above, if the hydrogen generator 213 is present (either from sodium formate or hydrogen gas), there may be quantities of H radicals or hydrogen gas), and as such, the MEK radical can react with these species (either in a radical reaction or in a hydrogen extraction reaction):

$$CH_3-C(O)-CH_2CH_2\bullet + H\bullet \longrightarrow$$
(MEK radical) (H radical)
$$CH_3-C(O)-CH_2CH_3$$
(MEK)

$$CH_3-C(O)-CH_2CH_2\bullet + H_2 \longrightarrow$$
(MEK radical) (hydrogen gas)
$$CH_3-C(O)-CH_2CH_3 + H\bullet$$
(MEK) (H radical)

Accordingly, this reaction produces MEK, which is shown in FIG. 2 as making up a portion of the product 271. In an embodiment, hydrogen gas may be introduced into the anolyte 228 such that it dissolves or forms a physical mixer in the anolyte. A significant concentration of hydrogen may be used at the electrode (anode 218) surface so that the above described reaction(s) may take place. Supplying excess hydrogen concentration in the anolyte 228 can be achieved by obtaining high hydrogen gas pressures, up to 250 PSI in one embodiment. In other embodiment utilizing a NASICON membrane tubular cell, pressures of about 3, 6, or 9 atmospheres may be used. Additionally, an embodiment utilizing a tubular cell may have a current density of 50 to 100 mA per square centimeter of membrane area.

Additionally, if H radicals (H.) are present in the system, such as from decarboxylation of formate or a hydrogen extraction process, these radicals can react together to form hydrogen gas:

$$H\bullet + H\bullet \longrightarrow H_2$$
(Hydrogen radical) (H radical) (Hydrogen gas)

Accordingly, this reaction can also produce hydrogen gas, which is also shown in FIG. 2 as making up a portion of the product 271.

Figure 3:
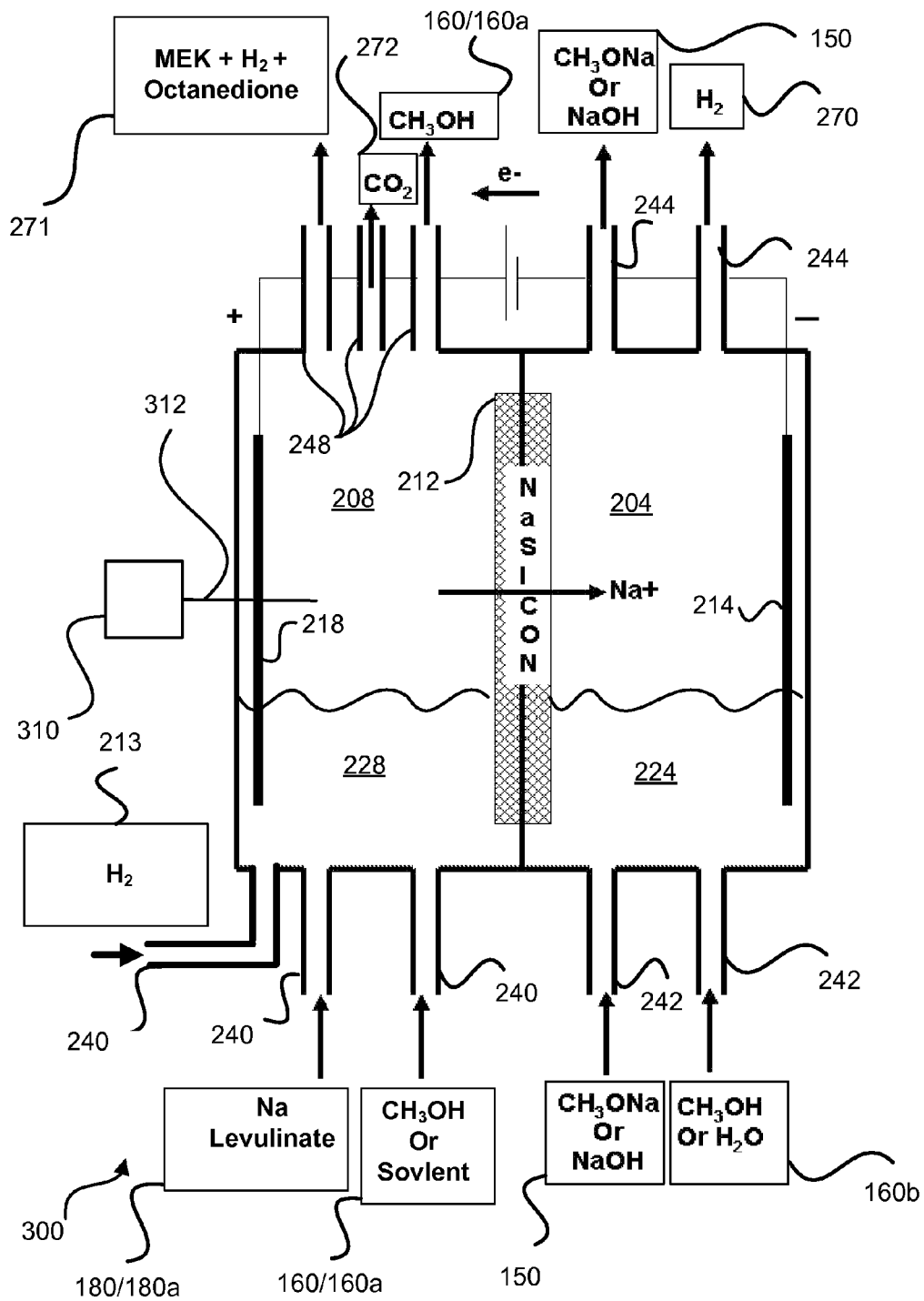
FIG. 3 is a schematic view of another embodiment of an electrolytic cell for conversion of sodium levulinate to MEK and other products.

Referring now to FIG. 3, an additional embodiment of a cell 300 is illustrated. The cell 300 is similar to the cells that have been previously described. Accordingly, for purposes of brevity, much of this discussion will not be repeated. In the embodiment of FIG. 3, the cell 300 is designed such that one or more photolysis reactions may occur in the anolyte compartment 208. Specifically, a photolysis device 310 is designed such that it may emit radiation 312 into the anolyte compartment 208. This radiation may produce hydrogen radicals (H.). The hydrogen supplier 213 may be supplied to the anolyte compartment 208 as hydrogen gas that may undergo a photolysis reaction:

$$H_2 \xrightarrow{\text{(photolysis)}} H\bullet + H\bullet$$

This photolysis process may be combined with the electrolysis process of the cell described above:

$$CH_3-C(O)-CH_2CH_2COONa \xrightarrow{\text{(electrolysis)}}$$
(sodium salt of levulinic acid)
$$CH_3-C(O)-CH_2CH_2\bullet + CO_2 + e^- + Na^+$$
(MEK radical)

The hydrogen radicals and the MEK radicals may then combine to form a mixture of products (discussed above):

$$H\bullet + CH_3-C(O)-CH_2CH_2\bullet \rightarrow CH_3-C(O)-$$
$$CH_2CH_3 + CH_3-C(O)-CH_2CH_2-CH_2CH_2-C$$
$$(O)-CH_3 + H_2$$

Alternatively, the photolysis device 310 may be used to conduct decarboxylation and to generate hydrocarbon radicals:

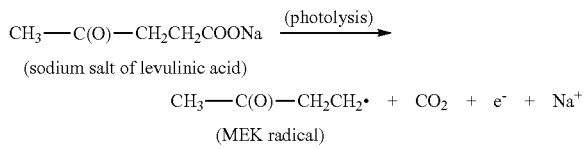

Thus, a combination of photolysis and electrolysis may be used to form the hydrocarbon radicals and/or hydrogen radicals in the anolyte compartment 208:

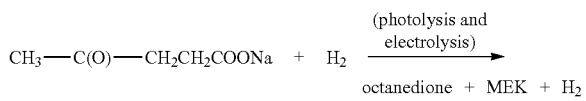

Yet additional embodiments may be designed using such photolysis techniques. For example, the following reactions may occur:

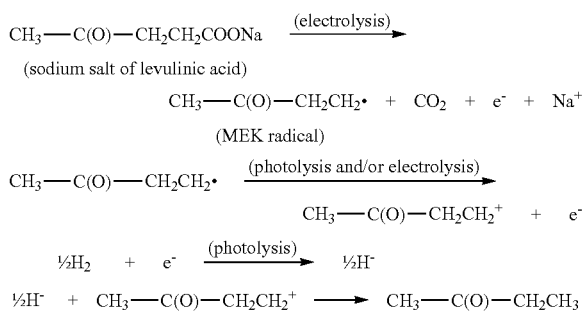

This combination of reactions (using photolysis and electrolysis) forms carbocations and H⁻ anions that may combine to form the hydrocarbon. Thus, photolysis may be used as a further mechanism for forming hydrocarbons.

It should be noted that additional information regarding photolysis reactions associated with levulinic acid (and/or sodium levulinate) may be found in the following article:

Chum, H. L, et. al., Photoelectrochemistry of Levulinic Acid on Undoped Platinized n-TIO₂ Powders, J. Phys. Chem. 1983, 87, 3089-3093.

Figure 4:
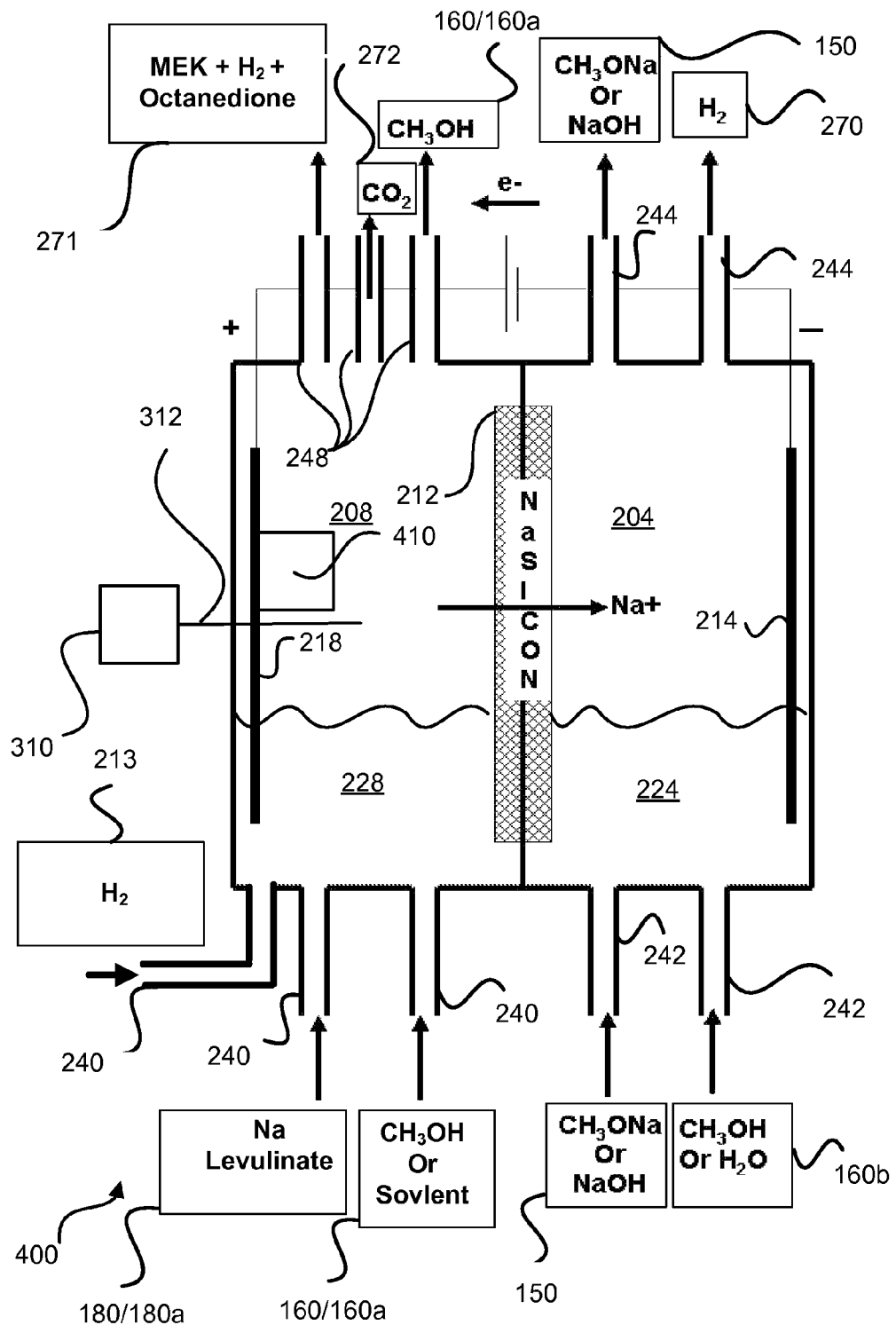
FIG. 4 is a schematic view of yet an embodiment of an electrolytic cell for conversion of sodium levulinate to MEK and other products.

An alternate embodiment to that of FIG. 4 will now be described with reference to the embodiment shown in FIG. 3. Because much of the embodiment of FIG. 4 is similar to that which is shown in FIG. 3, a discussion of portions of the similar features will be omitted for purposes of brevity, but is incorporated herein by this reference. The embodiment of FIG. 4 includes a cell 400 having an anolyte compartment 208 and a catholyte compartment 204. Because the anolyte compartment 208 is separate from the catholyte compartment 204, it is possible to create a reaction environment in the anolyte compartment 208 that is different from the catholyte compartment 204. FIG. 4 illustrates this concept. For example, hydrogen gas (H₂) may be used as the hydrogen suppler 213 and may be introduced into the anolyte compartment 208. The hydrogen gas may be pressurized within the cell because the NaSICON membrane can withstand high pressures (such as up to 250 PSI or even as high as 900 PSI). In some embodiments, the anolyte compartment 208 may be pressurized by hydrogen gas. In some embodiments, the anode 218 could include a component 410 made of Pd or other noble metal (such as Rh, Ni, Pt) or another substrate such as Si, a zeolite, etc. (This component may be all or part of the electrode.) This component 410 may be used separately or in addition to the photolysis device 310. The component 410 may alternatively be separate from the electrode. In further embodiments, Pd or Carbon with Pd could be suspended within the cell as a secondary anode or a non-electrochemical hydrogen activating catalyst. The effect of having hydrogen gas in the anolyte compartment 208 is that the hydrogen gas may form hydrogen radicals (H.) during the reaction process that react in the manner noted above. These radicals would react with the MEK radical so that the resulting products would be MEK and (other products such as octanedione). If sufficient hydrogen radicals (H.) are present, the MEK product would be predominant, or would be the exclusive product. This reaction could be summarized as follows (using Pd as an example of a noble metal, noting that any other noble metal could be used):

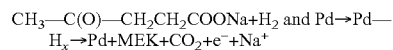

By using one or more of the noble metals with hydrogen gas in the anolyte compartment, the particular product (MEK) may be selected. In the embodiment of FIG. 4, hydrogen gas is produced in the catholyte compartment 204 as part of the reduction reaction. This hydrogen gas 270 may be collected and used as the hydrogen gas that is reacted with the noble metal in the anolyte compartment 208. Thus, the cell 400 actually may produce its own hydrogen gas 270 supply that will be used in the reaction. Alternatively, the hydrogen gas 270 that is collected may be used for further processing of the hydrocarbon, such as cracking and/or isomerizing waxes and/or diesel fuel. Other processing using hydrogen gas may also be performed.

It should be noted that the hydrogen supplier 213 that is used in the above-recited embodiments may include other chemicals/species that are capable of "donating" or "providing" a hydrogen to the MEK radical (CH₃—C(O)—CH₂CH₂.) in order to form MEK. These species may form hydrogen radicals (or other species) that can react with the MEK radical to form MEK. For example, emboidments may be constructed in which certain organic compounds (such as branched or unbranched alkanes) provide the hydrogen/proton to form the MEK radical. This process is illustrated by the following reaction:

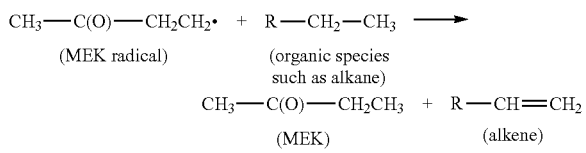

(In this embodiment, R represents a functional organic group.)

Further, the embodiment of FIG. 4 discloses the use of Pd or another metal as a means to form hydrogen radicals. Specifically, the embodiment of FIG. 4 uses hydrogen gas in conjunction with a component 410 made of Pd or another metal as a means of forming H radicals. It should be noted that further embodiments may be constructed in which the component 410 is absent, but that the anode itself is made of Pd (or another noble metal (such as Rh, Ni, Pt) or another substrate such as Si, a zeolite, etc.). In this embodiment, the electrode (anode 218) provides the metal that generates the H radicals. As known in the art, the Pd or noble metal provides a catalytic surface whereby the hydrogen may react, thereby aiding the reaction of the hydrogen. Another embodiment may use an electrochemical driving force in addition to a Pd metal anode 218 to facilitate hydrogen radical generation for use in a Pd and sodium levulinate reaction as described above.

It should be noted that the processes described herein whereby the MEK radical reacts with H to form MEK may be referred to as "hydrogen abstraction." In other words, the MEK radical "abstracts" a hydrogen from the hydrogen supplier 213 to form MEK. As described herein, the hydrogen abstraction may involve forming hydrogen radicals by completely terminating the H—H bond in hydrogen gas. Other forms of hydrogen abstraction may involve simply "weakening" the bond so that the MEK radical may react with one of the hydrogen species to form MEK. Other embodiments may be designed in which the hydrogen is abstracted from another species (such as an alkane) or $H_2O$, $CH_3OH$, etc.

Although not intended to be limited by any particular theory, it is believed that there are other different pathways that may be involved in formation of MEK under the present advanced "Kolbe" reaction. Four additional, possible pathways are outlined below:

Possible Pathway #1 (Methanol Solvent is the Source of the Proton)

$CH_3OH\ (solvent) \rightarrow CH_3O^- + H^+$

$CH_3OH\ (solvent) \rightarrow CH_3O^+ + H^-$

In turn, this proton or radical reacts to form MEK.

$CH_3$—$C(O)$—$CH_2CH_2COONa + H^+$ or $H^- \rightarrow CH_3$—$C(O)$—$CH_2CH_3+$ Possible Pathway #2 (Methanol Reacts to Form Acid from Sodium Levulinate)

It is possible that the sodium levulinate can react with the methanol solvent to form the levulinic acid, and then this acid undergoes the Kolbe reaction:

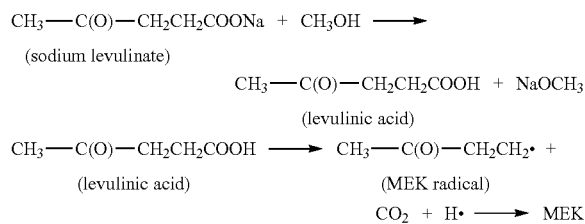

Possible Pathway #3 (Use of Water in Solvent)
It is possible that there may be a preference for water (which is found in the solvent) to cause generation of MEK.

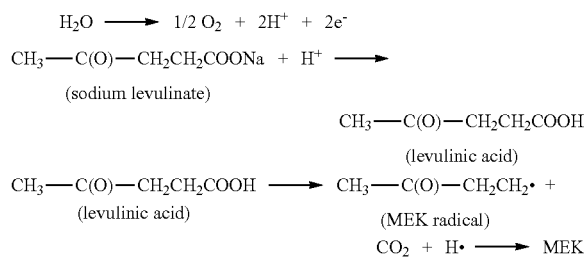

Possible Pathway #4 (Methanol Oxidation to Formic Acid)
It is possible that methanol solvent may be oxidized to formic acid in the cell

$2CH_3OH \rightarrow HCOOH + CH_4 + H_2$
(methanol)    (formic acid)   (methane)

Alternatively, the formic acid may be formed by reaction with $O_2$ (which is formed in the cell from water or methanol)

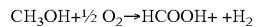
$CH_3OH + \frac{1}{2} O_2 \rightarrow HCOOH + H_2$

Once formed, this formic acid may undergo the Kolbe reaction to form hydrogen radicals:

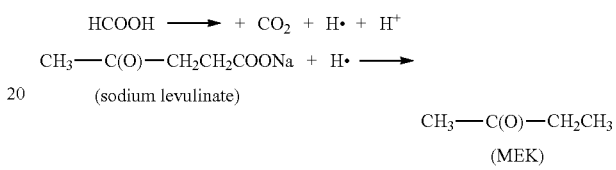

It should be noted that the embodiments of FIGS. 2-4 are designed in which there are two compartments to the cell. However, those skilled in the art will appreciate that embodiments may be constructed in which there is a single chamber (compartment) in the cell. In this embodiment, the hydrogen gas that is generated in the cathode would be used as the source of the hydrogen supplier.

Figure 5:
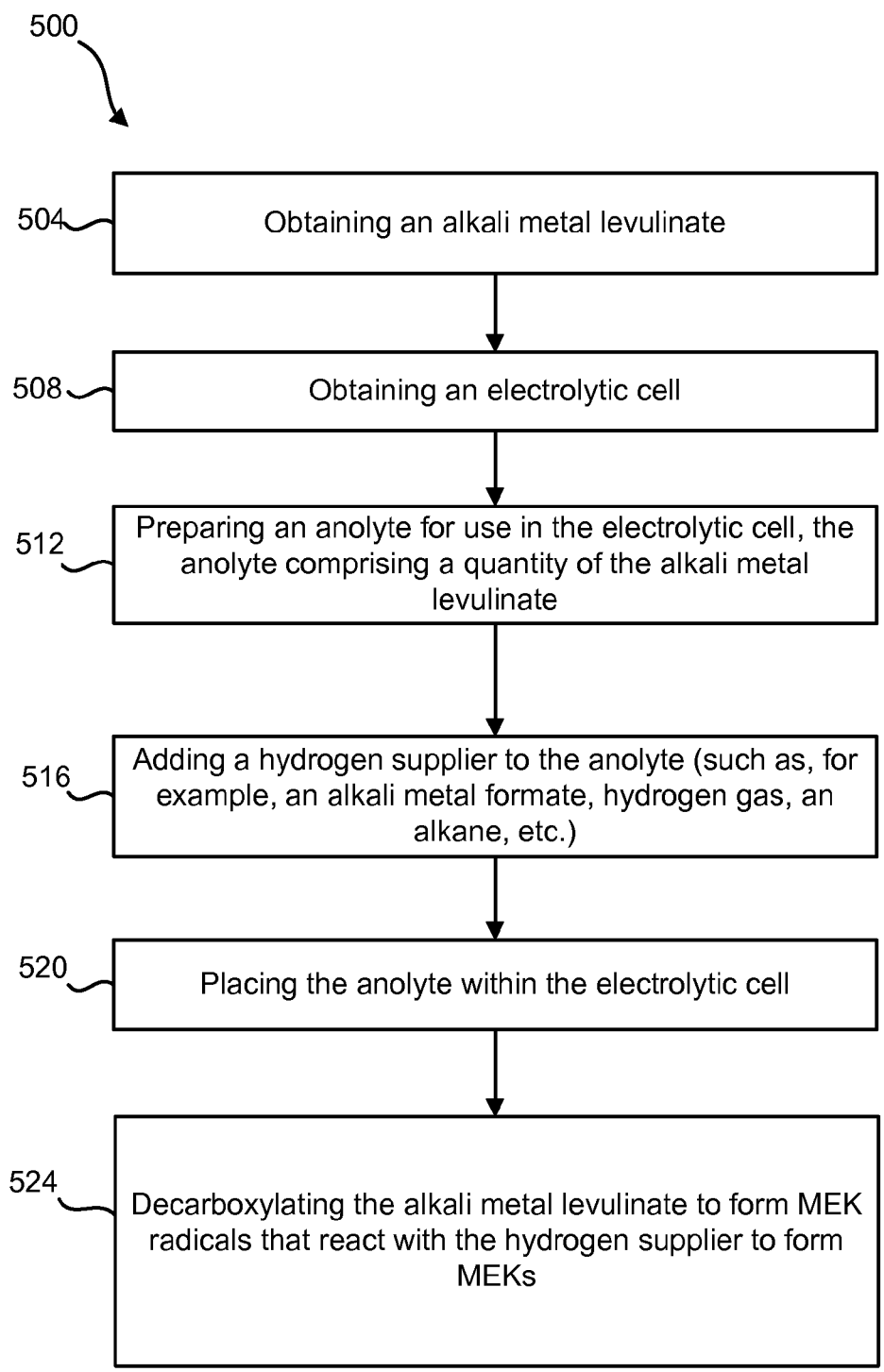
FIG. 5 is a flow diagram showing an exemplary method of the present embodiments.

Referring now to FIG. 5, a flow diagram is shown of a method 500 for producing MEK. The method 500 comprises obtaining 504 an alkali metal levulinate. As noted herein, this alkali metal levulinate may be obtained by converting a six carbon suger into levulinic acid and then reacting the levulinic acid with a base to obtain an alkali metal levulinate. Alternatively, this alkali metal levulinate may be purchased or otherwise obtained. The alkali metal levulinate may be a sodium salt (e.g., sodium levulinate).

An electrolytic cell will also be obtained 508. An anolyte is also prepared 512. The anolyte may be of the type described herein. Specifically, the anolyte comprises a quantity of the alkali metal levulinate. A hydrogen supplier will also be added 516 to the anolyte. As described in greater detail herein, the hydrogen supplier may comprise a quantity of an alkali metal formate (that was obtained from the six carbon sugar). The hydrogen supplier (additionally or alternatively) may comprise hydrogen gas. Other chemicals may also be used as the hydrogen supplier such as an alcohol (like methanol, ethanol, triglyceride, etc.), water, an alkane, etc.

Once prepared, the anolyte may be placed 520 in the electrolytic cell. The alkali metal levulinate may then be decarboxylated 524 in the electrolytic cell. This decarboxylation operates to convert the alkali metal levulinate into MEK radicals that may react with the hydrogen supplier to form MEK. As explained herein, this reaction of MEK radicals with the hydrogen supplier may involve abstracting the H from hydrogen gas, the alcohol, water, the alkane, etc. In other embodiments, H radicals are formed (via photolysis or via decarboxylation of formate) which may react with the MEK radicals.

Figure 6:
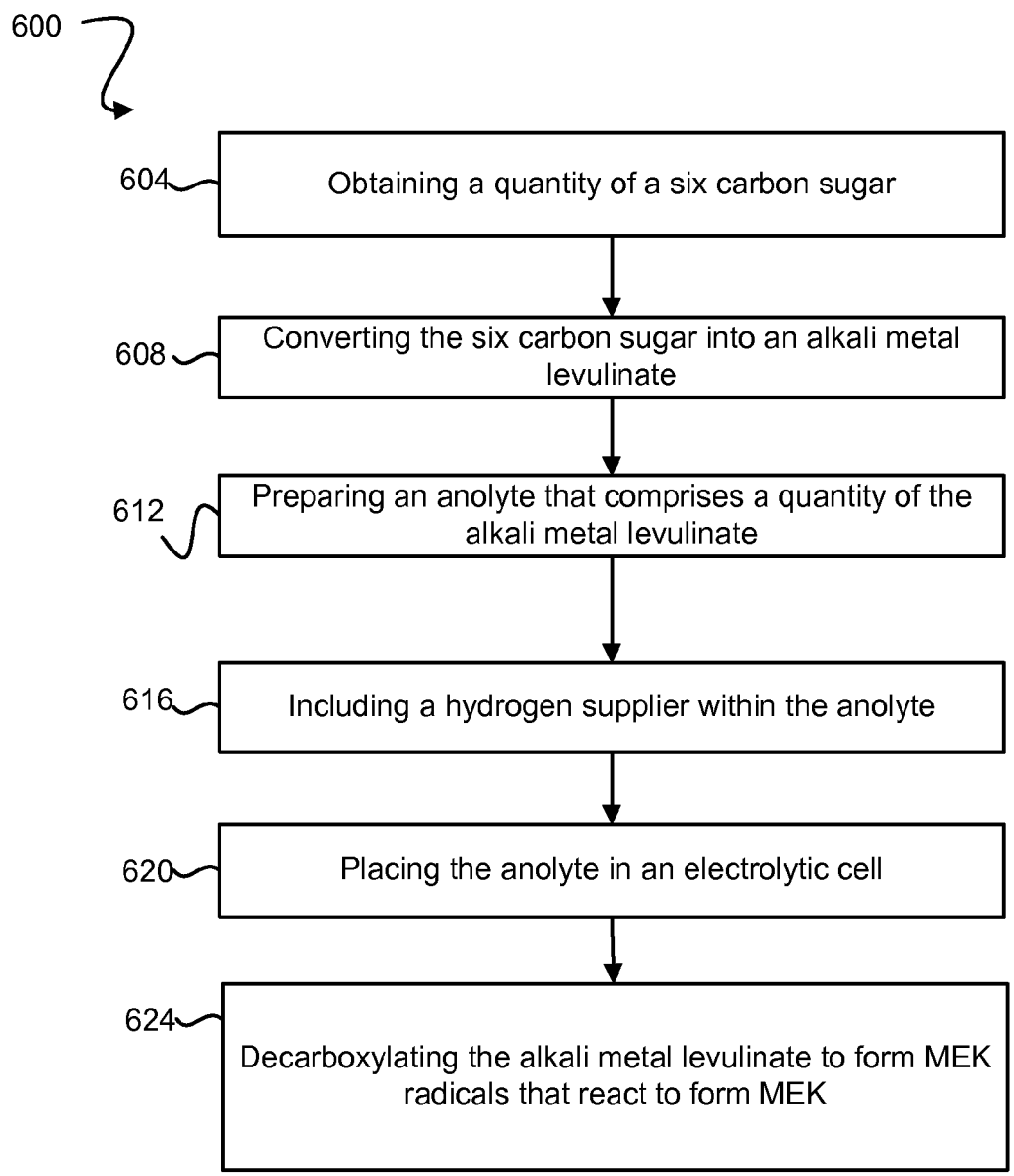
FIG. 6 is another flow diagram showing another exemplary method of the present embodiments.

Referring now to FIG. 6, another exemplary method 600 according to the present embodiments is illustrated. The method 600 may be used to form MEK. The method involves obtaining 604 a quantity of a six carbon sugar. Once obtained, the six carbon sugar is converted 608 into an alkali metal levulinate. As noted herein, this process may involve dehydrating the sugar to form levulinic acid and formic acid, and then reacting these acids with a base to form an alkali metal levulinate and an alkali metal formate. If the alkali metal is sodium, sodium levulinate and sodium formate are used.

An anolyte will then be prepared 612. The anolyte comprises a quantity of the alkali metal levulinate. A hydrogen supplier may also be included 616 in the anolyte. As noted herein, a variety of different materials may be used as the hydrogen supplier including hydrogen gas, formate, alkanes, water, alcohols, etc. Once prepared, the anolyte may be placed 620 in an electrolytic cell, such as those described herein.

After placing the anolyte in the cell, the alkali metal levulinate is decarboxylated 624. This decarboxylation may involve electrolysis and/or photolysis. Such decarboxylation forms one or more MEK radicals that react to form MEK. As explained herein, the MEK radicals may react with the hydrogen supplier (or H radicals or other species derived from the hydrogen supplier) to form MEK. It is anticipated that octanedione and hydrogen will be formed as co-products of such radical reactions. For example when MEK radicals react together 2,7-octanedione may be formed and when hydrogen radicals reacti together hydrogen gas may be formed as noted in the reaction scheme in paragraph 40 above.

All of the articles/papers mentioned in this disclosure are expressly incorporated herein by reference.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of forming a ketone comprising:
obtaining a quantity of a six carbon sugar;
reacting the sugar to form an alkali metal levulinate;
preparing an anolyte comprising the alkali metal levulinate;
decarboxylating the alkali metal levulinate within the anolyte in an electrolytic cell to form at least a methyl ethyl ketone ("MEK") radical, wherein the electrolytic cell comprises an anolyte compartment that houses the anolyte, a catholyte compartment that houses a catholyte, and an alkali ion conducting membrane that separates the anolyte compartment from the catholyte compartment, wherein the MEK radicals in the anolyte further react to form a ketone.

2. A method as claimed in claim 1, wherein the ketone is a MEK.

3. A method as claimed in claim 1, wherein the ketone is an octanedione.

4. A method as claimed in claim 2, wherein the anolyte further comprises a quantity of a hydrogen supplier that is used to form MEK.

5. A method as claimed in claim 2, wherein the hydrogen supplier comprises alkali metal formate, further comprising the steps of:
decarboxylating the alkali metal formate to form H radicals, wherein the H radicals react with the MEK radicals to form MEK.

6. A method as claimed in claim 5, wherein the alkali metal formate is formed from the six carbon sugar.

7. A method as claimed in claim 4, wherein the hydrogen supplier comprises a quantity of hydrogen gas.

8. A method as claimed in claim 7, wherein the MEK radicals react with the hydrogen gas to form MEK via a hydrogen abstraction process.

9. A method as claimed in claim 4, wherein the hydrogen supplier comprises an alkane, an alcohol or water.

10. A method as m claim 2, wherein the alkali ion conducting membrane is a NaSICON membrane.

11. A method as claimed in claim 2, wherein the electrolytic cell further comprises a photolysis device.

12. A method as claimed in claim 11, wherein the photolysis device decarboxylates the alkali metal salt of levulinate.

13. A method as claimed in claim 12, wherein the photolysis device creates hydrogen radicals that react with the MEK radicals to form MEK.

14. A method for producing methyl ethyl ketone ("MEK") comprising:
preparing an anolyte for use in an electrolytic cell, the electrolytic cell comprising an alkali ion conducting membrane, wherein the anolyte comprises a solvent and a quantity of an alkali metal levulinate; and
decarboxylating the alkali metal levulinate within the electrolytic cell, wherein the decarboxylating converts the alkali metal levulinate into MEK radicals that react to form MEK.

15. A method as in claim 14, wherein the decarboxylating the alkali metal levulinate occurs by electrolyzing the anolyte.

16. A method as in claim 14, wherein the alkali metal levulinate comprises a sodium levulinate and the alkali ion conducting membrane comprises a NaSICON membrane, wherein the membrane divides the cell into an anolyte compartment and a catholyte compartment, the anolyte being housed within the anolyte compartment and a catholyte being housed within the catholyte compartment.

17. A method as in claim 14, wherein the MEK radicals couple to hydrogen radicals.

18. A method as in claim 17, wherein the hydrogen radicals are formed by decarboxylating an alkali metal formate during either the decarboxylating of the alkali metal levulinate or photolysis of hydrogen gas or both.

19. A method for producing methyl ethyl ketone ("MEK") comprising:
obtaining sodium levulinate, the sodium levulinate derived from a six carbon sugar;
preparing an anolyte for use in an electrolytic cell, the electrolytic cell comprising an anolyte compartment, a catholyte compartment, and a NaSICON membrane that separates the anolyte compartment from the catholyte compartment, wherein the anolyte is housed within the anolyte compartment and a catholyte is housed within the catholyte compartment, wherein the anolyte comprises a solvent and a quantity of the sodium levulinate; and
electrolyzing the anolyte within the cell, wherein the electrolyzing decarboxylates the sodium levulinate and converts the sodium levulinate into one or more MEK radicals that react with a hydrogen supplier to form MEK.

20. An electrolytic cell comprising:
an anolyte compartment;
a catholyte compartment;
NaSICON membrane that separates the anolyte compartment from the catholyte compartment;
an anolyte is housed within the anolyte compartment, wherein the anolyte comprises a solvent, a hydrogen supplier and a quantity of sodium levulinate;

a catholyte is housed within the catholyte compartment; and a voltage supplier or photolysis device that decarboxylates the sodium levulinate and converts the sodium levulinate into one or more methyl ethyl ketone radicals that react with the hydrogen supplier to form methyl ethyl ketone.

21. An electrolytic cell as claimed in claim 20, wherein the cell comprising both a voltage supplier and a photolysis device.

22. An electrolytic cell as claimed in claim 21, wherein the photolysis device creates hydrogen radicals from the hydrogen supplier.

23. An electrolytic cell as claimed in claim 20, wherein the cell comprises a voltage supplier and does not include a photolysis device, wherein the hydrogen supplier comprises sodium formate, wherein the sodium formate is decarboxylated by the voltage supplier to form hydrogen radicals that react with the methyl ethyl ketone radicals to form methyl ethyl ketone.

* * * * *